(12) United States Patent
Van Dijk et al.

(10) Patent No.: US 9,919,485 B2
(45) Date of Patent: Mar. 20, 2018

(54) CAST MOULD AND METHOD FOR MANUFACTURING CONTACT OR INTRAOCULAR LENSES

(75) Inventors: Emerentius Maria Josephus Antonius Van Dijk, Eindhoven (NL); Joery Johannes Sinkeldam, Eindhoven (NL)

(73) Assignee: INNOVALENS B.V., Eindhoven (NL)

( * ) Notice: Subject to any disclaimer, the term of this patent is extended or adjusted under 35 U.S.C. 154(b) by 1050 days.

(21) Appl. No.: 14/124,638

(22) PCT Filed: Jun. 11, 2012

(86) PCT No.: PCT/NL2012/050404
§ 371 (c)(1),
(2), (4) Date: May 9, 2014

(87) PCT Pub. No.: WO2012/169894
PCT Pub. Date: Dec. 13, 2012

(65) Prior Publication Data
US 2014/0252667 A1    Sep. 11, 2014

(30) Foreign Application Priority Data
Jun. 9, 2011 (NL) .................................... 2006921

(51) Int. Cl.
*B29D 11/00* (2006.01)
*B29C 33/30* (2006.01)
(Continued)

(52) U.S. Cl.
CPC .......... *B29D 11/00528* (2013.01); *A61F 2/16* (2013.01); *B29C 33/303* (2013.01);
(Continued)

(58) Field of Classification Search
None
See application file for complete search history.

(56) References Cited

U.S. PATENT DOCUMENTS 3,806,079 A    4/1974    Beattie
4,761,069 A *  8/1988    Truong .................... G02C 7/04
                                                         249/134
(Continued)

FOREIGN PATENT DOCUMENTS

CN    101094765 A    12/2007
CN    101380802 A     3/2009
(Continued)

*Primary Examiner* — Matthew Daniels
*Assistant Examiner* — Manley L Cummins, IV
(74) *Attorney, Agent, or Firm* — Birch, Stewart, Kolasch & Birch, LLP

(57) ABSTRACT

A cast mold for manufacturing a contact lens or an intraocular lens, wherein the cast mold is provided with a central part and a bearing ring and a flexible connection between the central part and the bearing ring. Further, an injection mold is provided for manufacturing such a cast mold and a method for manufacturing such a cast mold. The injection mold is provided with a mold cavity with a plunger biased by a spring towards the mold cavity which serves for compensating shrinkage which occurs during the curing of the plastic injected into the injection mold. Also described is a method for manufacturing a contact lens or intraocular lens with the aid of the cast mold, as well as a contact lens or intraocular lens obtained with this method.

14 Claims, 10 Drawing Sheets

(51) Int. Cl.
  *B29C 45/00* (2006.01)
  *B29C 45/57* (2006.01)
  *B29C 33/40* (2006.01)
  *A61F 2/16* (2006.01)
  *G02B 1/04* (2006.01)
  *B29L 11/00* (2006.01)

(52) U.S. Cl.
  CPC .......... *B29C 33/40* (2013.01); *B29C 45/0081* (2013.01); *B29C 45/572* (2013.01); *B29D 11/005* (2013.01); *B29D 11/00567* (2013.01); *G02B 1/043* (2013.01); *B29L 2011/0041* (2013.01)

(56) References Cited

U.S. PATENT DOCUMENTS

| | | | |
|---|---|---|---|
| 5,540,410 | A | 7/1996 | Lust et al. |
| 5,620,720 | A | 4/1997 | Glick et al. |
| 6,368,522 | B1 * | 4/2002 | Ansell ................ B29C 33/0055 264/1.1 |
| 2003/0049342 | A1 | 3/2003 | Foreman et al. |
| 2006/0145370 | A1 * | 7/2006 | Lawton ............... B29C 45/2675 264/1.32 |
| 2007/0035051 | A1 | 2/2007 | Darnton et al. |
| 2007/0115428 | A1 | 5/2007 | Lin |
| 2009/0166507 | A1 | 7/2009 | Lawton et al. |

FOREIGN PATENT DOCUMENTS

| | | |
|---|---|---|
| CN | 101791864 A | 8/2010 |
| EP | 0367513 A2 | 5/1990 |
| FR | 1355774 A | 3/1964 |
| GB | 2 050 928 A | 1/1981 |
| JP | 54-148055 A | 11/1979 |
| JP | 55-158949 A | 12/1980 |
| JP | 63-160813 A | 7/1988 |
| JP | 2002-273732 A | 9/2002 |
| JP | 2003-71874 A | 3/2003 |
| JP | 2007-47805 A | 2/2007 |
| JP | 2011-508284 A | 3/2011 |
| NL | 1033905 C | 12/2008 |
| WO | WO 00/59713 A1 | 10/2000 |

\* cited by examiner

CAST MOULD AND METHOD FOR MANUFACTURING CONTACT OR INTRAOCULAR LENSES

FIELD OF THE INVENTION

The invention relates to a cast mould for the purpose of manufacturing a contact lens or an intraocular lens. The invention further relates to a method for manufacturing such a cast mould. The invention also relates to an injection mould for use with this method. The invention further relates to a method for manufacturing a contact lens or an intraocular lens with the aid of the cast mould and to a contact lens or an intraocular lens obtained with this method.

BACKGROUND

A cast mould for the purpose of manufacturing contact lenses or intraocular lenses is described in, for instance, NL1033905C, EP-A-0 367 513 or in US 2009/0166507 A1. The cast mould known from NL1033905C is provided with a first cast mould half comprising an optically accurately defined surface and first positioning means. The known cast mould is further provided with a second cast mould half comprising a central part with optically accurately defined surface, a bearing ring that surrounds the central part and is provided with second positioning means which are designed for engagement of the first positioning means in a closed position of the cast mould in which the first and the second cast mould halves are placed on top of each other. For the purpose of manufacturing a contact lens or intraocular lens, a monomer material is introduced into one of the two cast mould halves and then the second cast mould half is placed on the first cast mould half. Subsequently, the monomer material will polymerize.

In NL1033905C, it is described that the positioning means can be designed for fastening the second cast mould half onto the first cast mould half and for keeping these in use on top of one another under a bias.

From NL1033905C and EP-A-0 367513 it is also known to use one of the mould halves as part of a package with which the lens can then be put on the market.

With regard to the manner of manufacture of plastic cast moulds nothing of relevance is disclosed in the publications mentioned. In this respect, more can be learned from U.S. Pat. No. 5,540,410. In particular FIG. 5 from this publication with the associated description in column 10, line 38-column 14, line 3 is especially clarifying and is therefore understood to be incorporated herein by reference. US 2006/145370 too discloses a method and an injection mould for injection moulding a cast mould. The injection mould is provided with optical tool inserts which are detachably attached in an element that is attached in the injection mould half. FR-1.355.774 describes in general terms the problem of the formation of bubbles and shrinkage cavities when the injected plastic cures in an injection mould. The French publication also describes how this shrinkage can be compensated for by using a mechanically or hydraulically energized piston which is pressed into the injection mould cavity during curing.

SUMMARY OF THE INVENTION

Although the cast mould described in NL1033905C with positioning means with which the second cast mould half can be fastened onto the first cast mould half is particularly favourable in view of the simple manner in which the cast mould halves can be held pressed on top of one another under a bias by the positioning means without requiring external mechanisms to that end, still, a problem has been observed with regard to the accuracy of the optical surfaces of the contact lens or the intraocular lens that can be manufactured with this known cast mould.

An objective is to provide a cast mould for a contact lens or an intraocular lens which solves or at least considerably reduces the accuracy problems indicated hereinabove.

To that end, the invention provides a cast mould for the purpose of manufacturing a contact lens or an intraocular lens, the cast mould being provided with:
  a first cast mould half comprising:
    an optically accurately defined surface;
    first positioning means:
  a second cast mould half comprising:
    a central part with optically accurately defined surface;
    a bearing ring which surrounds the central part and which is provided with second positioning means which are designed for engagement of the first positioning means for holding the cast mould under a bias in a closed position in which the first and the second cast mould halves are clamped onto each other, wherein a central axis of the second cast mould half extends perpendicularly to the plane in which the bearing ring extends and intersects a centre of the bearing ring; and
  characterized by:
    a thin-walled, flexible connection which extends between the bearing ring and the central part and which connects the central part with the bearing ring.

It has appeared that the above-mentioned inaccuracy is caused by deformation of the optically accurately defined surfaces which occurs as a result of the material stress that is introduced into the material when the positioning means are brought in the position engaging one another. In order to be able to generate the required bias or clamping force, the positioning means have to be brought into a deformed condition. However, this deformation appeared not to limit itself to the positioning means only but also to continue into the optically accurately defined surfaces.

The cast mould according to the invention offers the advantage that the central part thereof can be of rigid design so that during the manufacture of a lens, in this cast mould, no deformation of the optically accurately defined surfaces occurs. The thin-walled, flexible connection provides that the material stresses that occur in the positioning means do not continue into the central part with the optically accurately defined surface.

In one embodiment, the thin-walled, flexible connection has a wall thickness of less than 0.2 times the thickness of the bearing ring. Preferably, the wall thickness of the flexible connection is less than 0.1 times the thickness of the bearing ring.

When the wall thickness of the thin-walled, flexible connection is related to the thickness of the central part at the location of the central axis of the second cast mould, it may hold in one embodiment that the wall thickness of the thin-walled, flexible connection is less than 0.2 times the thickness of the central part at the location of the central axis and preferably even less than 0.1 times the thickness of the central part at the location of the central axis. With such a ratio between the thickness of the thin-walled flexible connection and the thickness of the central part, deformation of the central part as a result of clamping forces generated or experienced by the positioning means is effectively prevented.

Manufacturing such a cast mould from plastic by means of injection moulding is not straightforward. Especially the second cast mould half forms a problematic part. An injection mould for manufacturing the second cast mould half is provided with an injection mould cavity which is provided with a central part cavity, a bearing ring cavity, and a connecting cavity which connects the central part cavity to the bearing ring cavity. In the connecting cavity, the thin-walled, flexible connection which extends between the bearing ring and the central part of the second cast mould half is formed. The plastic that is injected during the injection moulding must pass this connecting cavity to reach the central part cavity. As the connecting cavity is very flat and has a relatively large surface relative to the content thereof, setting of the plastic will occur fairly quickly there. As a result, refilling of the central part cavity with plastic is no longer possible even if the extruder still exerts pressure on the plastic. Upon shrinkage of the plastic in the injection mould, release of the plastic from the optically accurately defined surface of the injection mould can occur and through cavitation bubbles can form in the second cast mould half to be formed. This type of phenomena therefore leads to a second injection mould half with a non-accurately defined optical surface.

In order to solve this problem, the invention provides a method for manufacturing at least the second cast mould half of a cast mould according to the invention, the method comprising:

presenting an injection mould which is provided with
  a first injection mould half;
  a second injection mould half;
  wherein the two injection mould halves, in a moved together, closed position, define at least one injection mould cavity for manufacturing the second cast mould half, each injection mould cavity being provided with:
    a central part cavity;
    a bearing ring cavity which surrounds the central part cavity; and with
    a connecting cavity which connects the central part cavity to the bearing ring cavity;
  wherein the injection mould for each injection mould cavity thereof is provided with:
    a plunger, associated with the injection mould cavity, which is set up in the first injection mould half so as to be movable along a central axis of the plunger, the plunger being provided with an end face facing the injection mould cavity and bounding the central part cavity; and with
    spring means associated with the injection mould cavity which are under a bias such that the spring action thereof urges the plunger in the direction of the central part cavity towards a pressed-in condition;
the method further comprising:
  bringing the two injection mould halves into the closed position;
  injecting plastic into the at least one injection mould cavity at a pressure which is such that the plunger is moved from the pressed-in position against spring action;
  ending the injection and then allowing the plastic to cure while the spring means continuously urge the plunger in the direction of the central part cavity to compensate for shrinkage of the plastic in the central part cavity.

The invention further provides an injection mould for use with this method for forming at least a second cast mould half of a cast mould according to the invention, wherein the injection mould is provided with:

a first injection mould half;
  a second injection mould half
  at least one injection mould cavity for manufacturing the second injection mould half which is formed when the two injection mould halves are in a moved together, closed position, wherein each injection mould cavity is provided with:
    a central part cavity
    a bearing ring cavity; and with
    a connecting cavity which connects the central part cavity to the bearing ring cavity;
  wherein the injection mould for each injection mould cavity is provided with:
    a plunger associated with the injection mould cavity, which is set up in the first injection mould half so as to be movable along a central axis of the plunger, the plunger being provided with an end face facing the injection mould cavity and bounding the central part cavity; and with
    spring means associated with the injection mould cavity, which are under a bias such that the spring action thereof urges the plunger in the direction of the central part cavity towards a pressed-in position.

Through the presence of the plunger and spring means present per injection mould cavity, such a method and injection mould offer a solution to the shrinkage problems when manufacturing the second cast mould half of a cast mould for the purpose of contact lens or intraocular lens manufacture, which is provided with a flexible, thin-walled connection between the central part and the bearing ring. After the plastic in the connecting cavity has set and in the central part cavity the plastic is still liquid and undergoes shrinkage, the volume of the central part cavity is continuously reduced by the plunger and the spring means and thereby adapted to the decreasing volume of the setting plastic. Thus, it is ensured that the plastic remains in abutment against the injection mould surfaces and bubble formation resulting from cavitation is prevented. Thus, an accurately defined and undamaged surface of the optically accurate surface of the second cast mould halve is actually guaranteed.

The invention also provides a method for manufacturing a contact lens or an intraocular lens comprising:
  providing a first cast mould half of a cast mould according to the invention;
  using the method according to any one of claims 6-7 utilizing the injection mould according to any one of claims 8-11 for obtaining a second cast mould half of the cast mould according to the invention;
  filling the first cast mould half with a plastic;
  placing the second cast mould half on the first cast mould half such that the second positioning means engage the first positioning means and then clamp the second cast mould half on the first cast mould half under a bias;
  allowing the plastic to cure in the cast mould for forming the lens;
  removing the second cast mould half; and
  sealing with a seal the first cast mould half in which the lens is located for forming a package from the first cast mould half and the seal in which package the lens is included.

As a result of the high optical accuracy of the cast mould, the contact lens or intraocular lens obtained therefrom will be of high quality too. Furthermore, the lens is directly packaged in the first cast mould half. The risk of contamination or damage of the lens through manipulation of the lens is thus minimized.

In one embodiment, prior to applying the seal, a liquid can be introduced into the first cast mould half. Especially for soft lenses, creating a moist environment in the package is of importance for rendering and keeping the lens supple.

Finally, the invention relates to a contact lens or an intraocular lens manufactured with the method according to claim 13 or 14 utilizing a cast mould according to any one of claims 1-5.

Owing to the high optical accuracy of the optical surface of the cast mould, the optical quality of the contact lens obtained therewith is also better than that of the contact lenses and intraocular lenses known to date.

DETAILED DESCRIPTION

Figure 1:
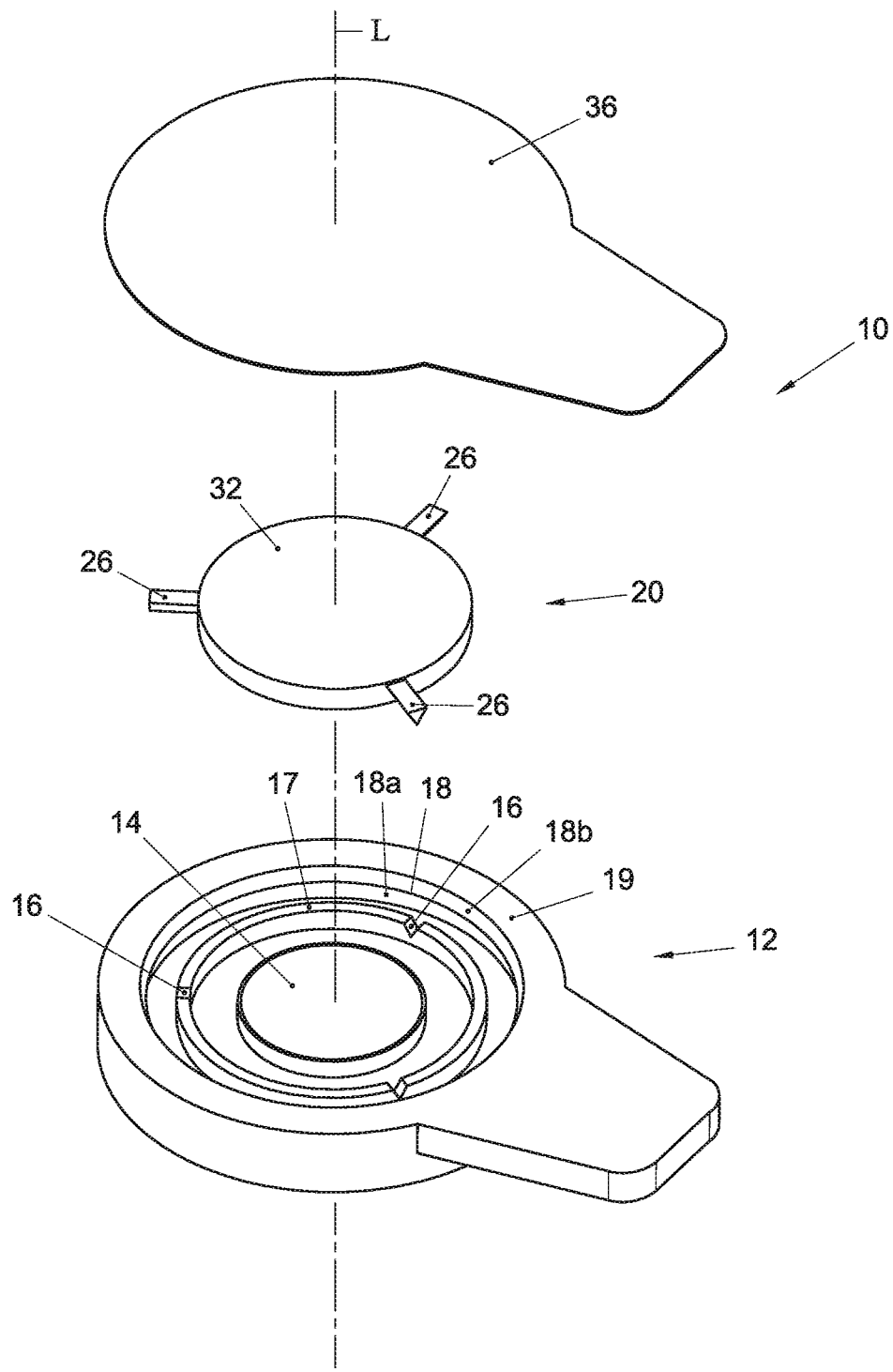
FIG. 1 shows in perspective from a first viewpoint an exemplary embodiment of a cast mould in exploded view which is intended for manufacture of a contact lens.
Figure 2:
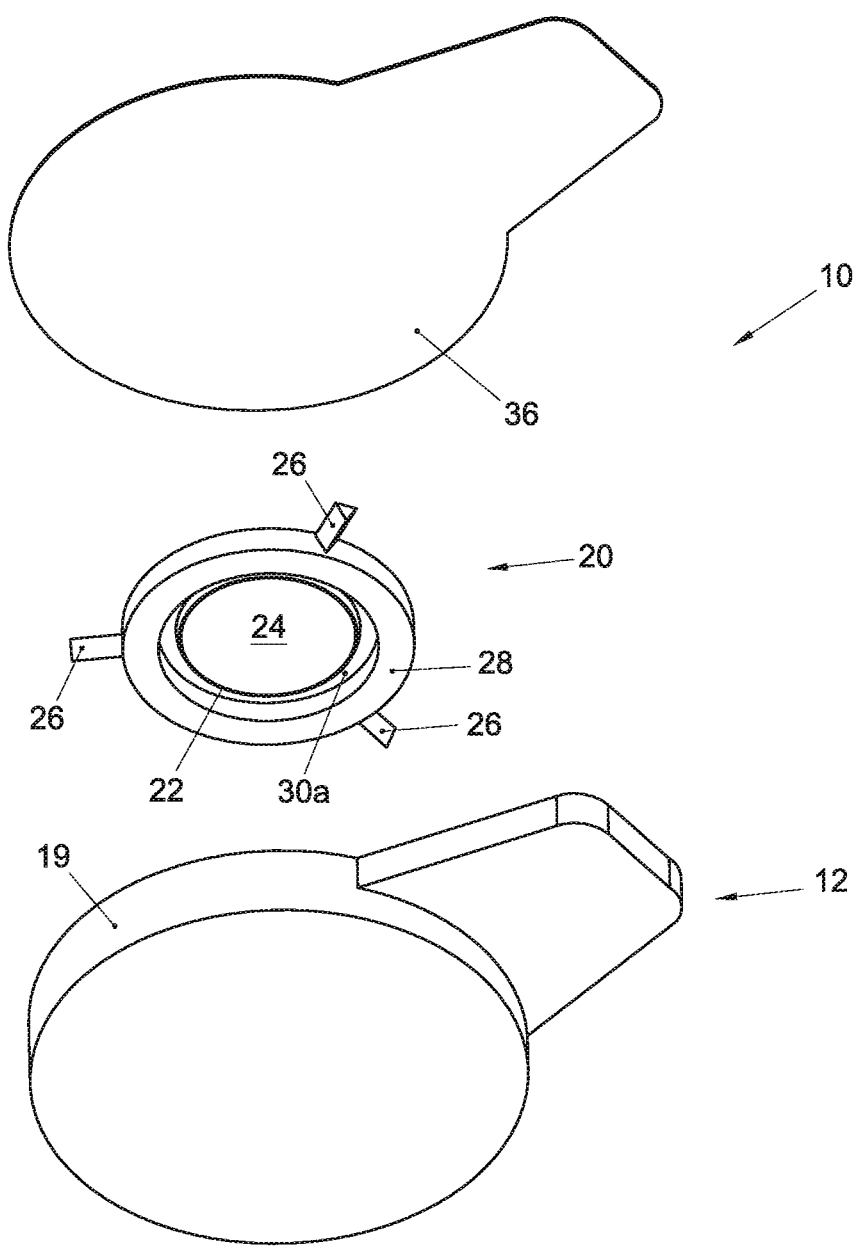
FIG. 2 shows the exemplary embodiment of the cast mould of FIG. 1 in exploded view from a second viewpoint.
Figure 3:
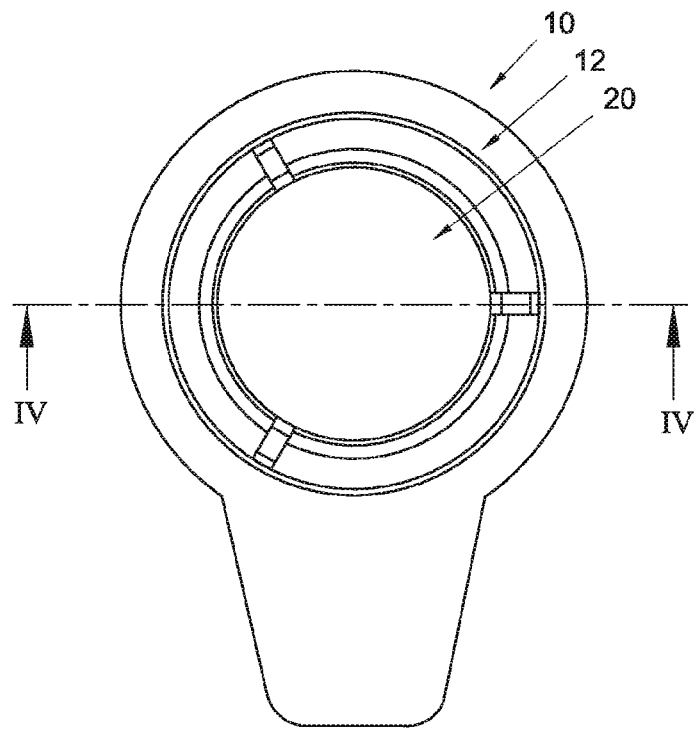
FIG. 3 shows the exemplary embodiment of the cast mould of FIG. 1 in top plan view.
Figure 4:
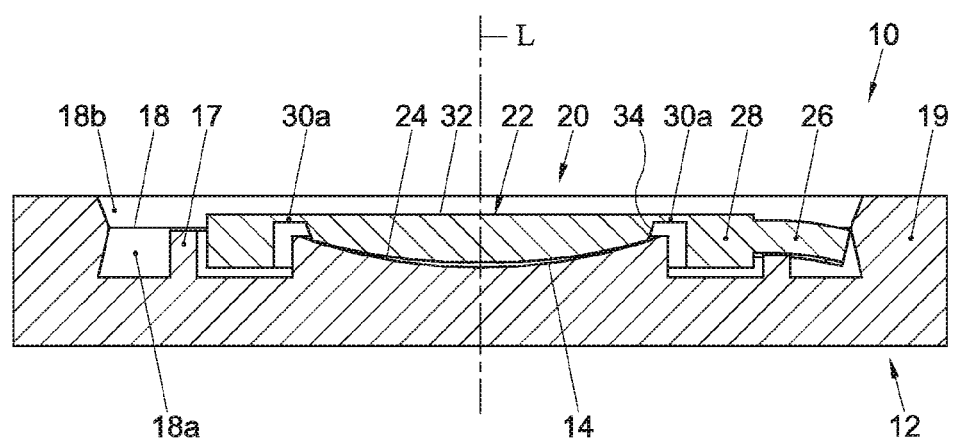
FIG. 4 shows a cross-sectional view along the line IV-IV of FIG. 3.

FIGS. 1-4 show an exemplary embodiment of the cast mould 10 for the purpose of manufacturing a contact lens. The cast mould 10 is provided with a first cast mould half 12. The first cast mould half 12 has an optically accurately defined surface 14 and first positioning means 16-18. In the exemplary embodiment, the first positioning means 16-18 are designed as recesses 16 in a substantially circular support rib 17 which surrounds the optically accurately defined surface 14, and a substantially circular clamping edge 18 which extends around the circular support rib 17 and which forms an integral part of an outer edge 19. On both sides of the clamping edge 18 extend, viewed from the clamping edge 18, radially outwardly widening annular surfaces 18a, 18b, which form an integral part of the outer edge 19 and which enable centring of the second cast mould half 20 with respect to the first cast mould half 12. However, in an alternative elaboration, the first positioning means 16-18 can also be configured as protuberances or projections.

The cast mould 10 is further provided with a second cast mould half 20. The second cast mould half 20 is provided with a central part 22 with an optically accurately defined surface 24. The second cast mould half 20 further has a bearing ring 28 which surrounds the central part 22 and which is provided with second positioning means 26. The second positioning means 26 are designed for engagement of the first positioning means 16-18 in a closed position of the cast mould 10, in which the first and the second cast mould halves 12, 20 are placed on top of one another, and wherein the first and the second positioning means 16-18, 26 in the mutually engaging condition generate a clamping force which presses the second cast mould half 20 onto the first cast mould half 12 under a bias. In the exemplary embodiment shown, the second positioning means 26 are designed as legs extending in radial direction. In this exemplary embodiment, the clamping force is generated by bending of the legs 26 which rest by a radially inwardly located portion in the recesses 16 of the support rib 17 and are snapped by a radial outer end under the clamping edge 18, to which end the legs 26 have to be bent. The positioning means 16-18 have the function not only of centring the two cast mould halves 12, 20 relative to each other and clamping them onto each other, but also of defining the relative rotational position of the two cast mould halves 12, 20.

A central axis L of the second cast mould 20 extends perpendicularly to the plane in which extends the bearing ring 28, and intersects a centre of the bearing ring 28. The second cast mould half 20 is provided with a thin-walled, flexible connection 30 which extends between the bearing ring 28 and the central part 22 and which connects the central part 22 to the bearing ring 28.

In a first embodiment of the second cast mould half 20, of which an example is shown in FIGS. 1-4, the flexible connection 30 can be configured as an annular plastic film 30a which is connected by an outer edge thereof to the bearing ring 28 and which is connected, by an inner edge thereof to the central part 22. Such a film connection provides good flexibility and hence freedom of movement of the central part 22 relative to the bearing ring 28, which is of importance for not transmitting material stresses, which occur when clamping the second cast mould half 20 onto the first cast mould half 12, to the accurately defined optical surface 24 of the second cast mould half 20. An elaboration with an annular plastic film 30a yet offers a considerable through-flow surface, which is important for the supply of plastic from the bearing ring cavity to the central part cavity in the injection mould 50 during the manufacturing process. Furthermore, the transmission of forces over the entire circumference of the central part 22 to the bearing ring 28 is uniform, which results in minimal deformation of the central part 22 under the influence of forces applied thereto during the lens manufacturing process.

Figure 5:
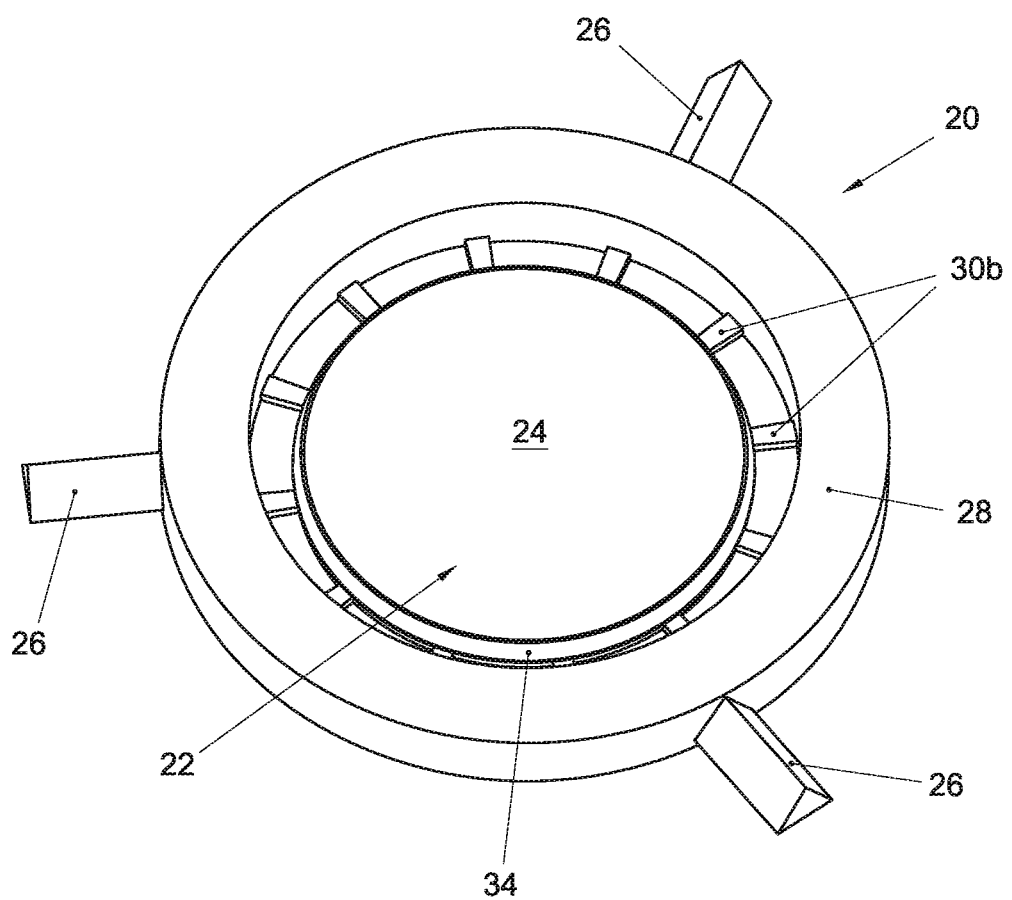
FIG. 5 shows a perspective view of a second exemplary embodiment of the second cast mould half.
Figure 6:
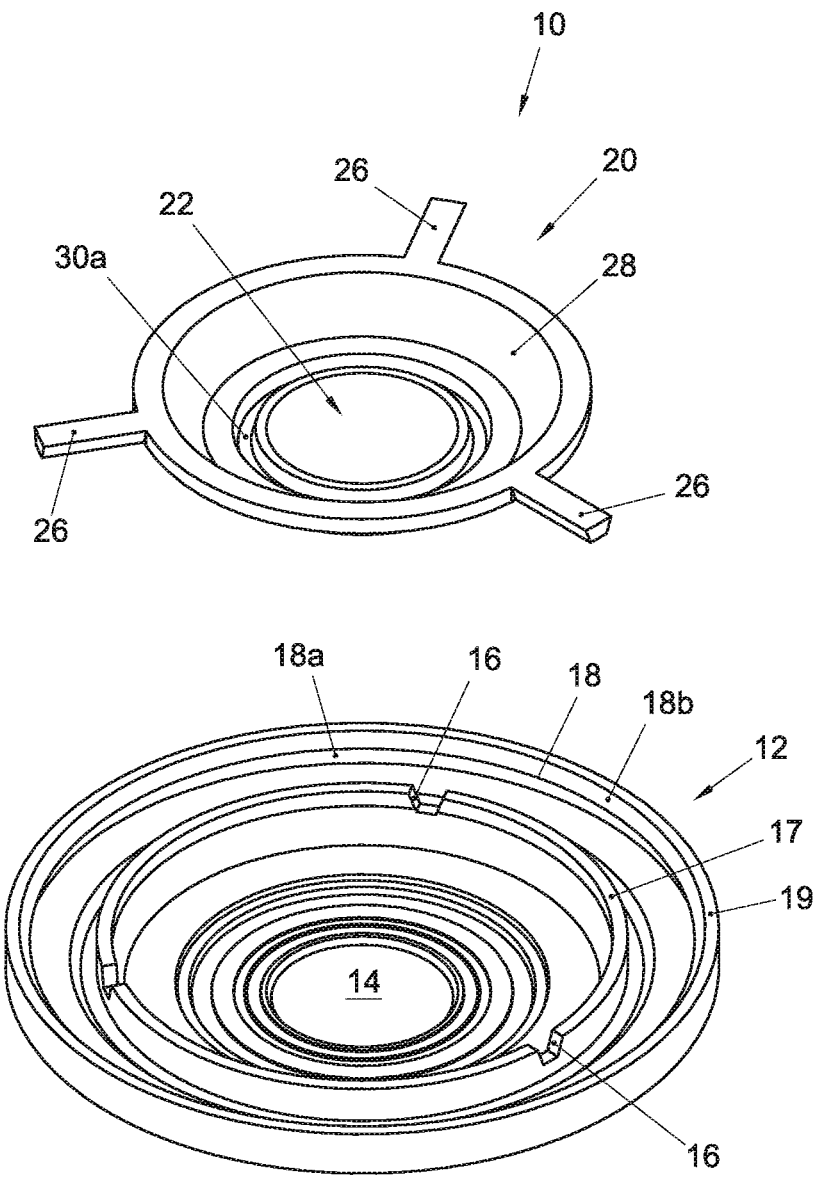
FIG. 6 shows a perspective view of a second exemplary embodiment of a cast mould which is intended for manufacture of an intraocular lens.
Figure 7:
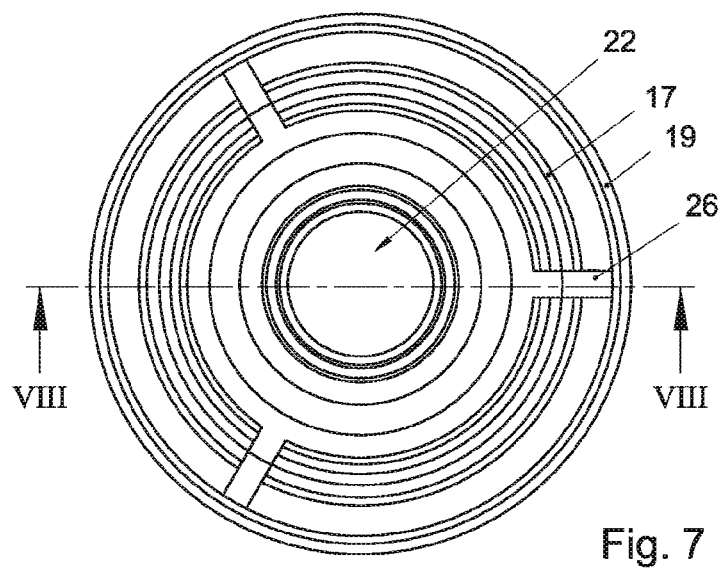
FIG. 7 shows a top plan view of the exemplary embodiment of a cast mould shown in FIG. 6.
Figure 8:
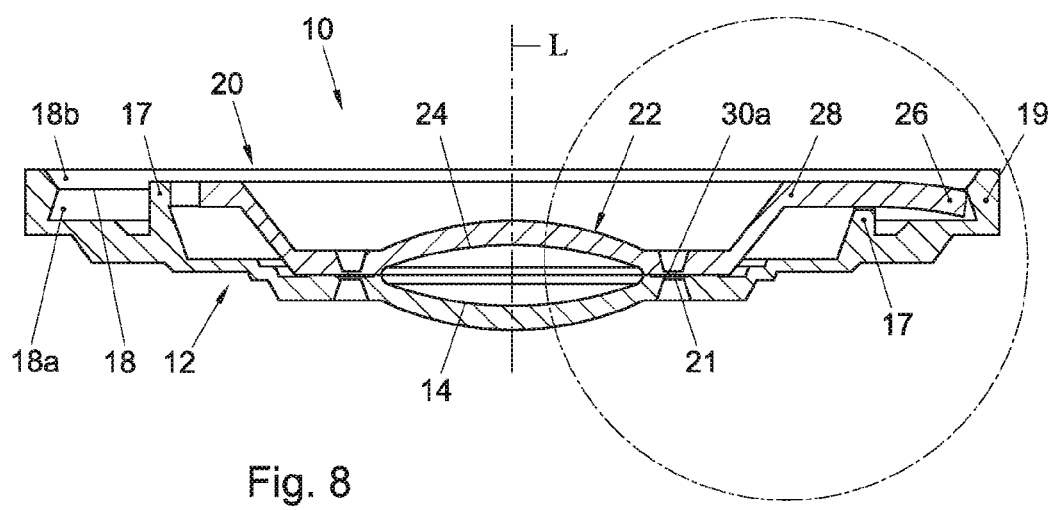
FIG. 8 shows a cross-sectional view along the line VIII-VIII of FIG. 7.
Figure 9:
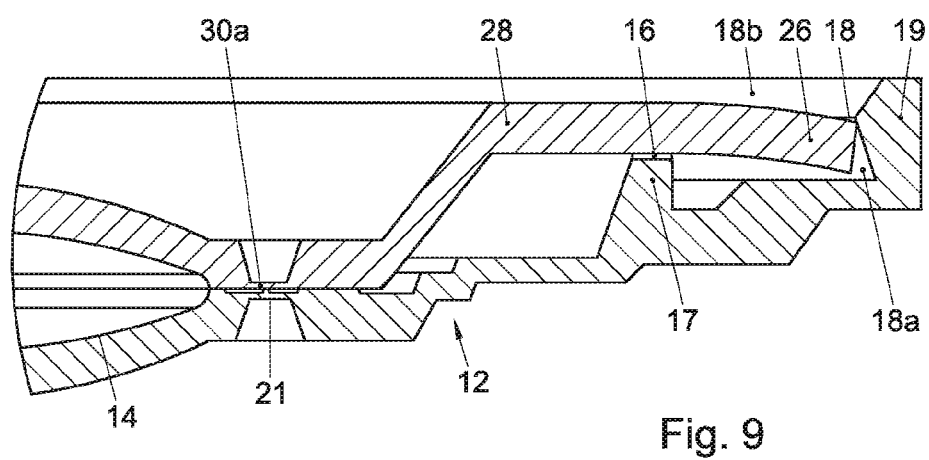
FIG. 9 shows detail IX of FIG. 8.

In a second alternative embodiment of the second cast mould half 20, of which an example is shown in FIG. 5, the flexible connection 30 can be implemented by a number of spokes 30b which are each connected by a first end to the central part 22 and are connected by a second end to the bearing ring 28. The spokes can extend radially from the central part 22 to the bearing ring 28. However, in an alternative embodiment, it is also possible that the spokes extend somewhat in tangential direction.

In one embodiment, the thin-walled, flexible connection 30, 30a, 30b has a wall thickness that is less than 0.2 times the thickness of the bearing ring 28. Preferably, the wall thickness of the flexible connection 30, 30a, 30b is less than 0.1 times the thickness of the bearing ring.

When the wall thickness of the thin-walled, flexible connection 30, 30a, 30b is related to the thickness of the central part 22 at the location of the central axis of the second cast mould half 20, it holds in one embodiment that the wall thickness of the thin-walled, flexible connection 30, 30a, 30b is less than 0.2 times the thickness of the central part 22 and preferably even less than 0.1 times the thickness of the central part 22 at the location of the central axis.

Opposite the optically accurately defined surface 24, the central part 22 of the second cast mould 20 is provided with a second main surface 32 which extends substantially perpendicularly to the central axis L of the second cast mould 10. The central part 22 is further provided with a circumferential surface 34 which extends between the optically accurately defined surface 24 and the second main surface 32. One embodiment is characterized in that the circumferential surface 34 is chamfered, such that a diameter of the central part 22, viewed in the direction of the central axis L, gradually decreases from the second main surface 32 to the optically accurately defined surface 24.

Without the chamfered configuration of the circumferential surface 34—i.e. with a circumferential surface extending perpendicularly to the second main surface 32—a deviation occurs in the perimeter of the optically accurately defined surface 24 during the manufacture of the second cast mould half 20. This deviation seems to be the result of a cooling effect near this perimeter. It appears that the deviation in the perimeter can be considerably reduced by the chamfered configuration of the circumferential surface 34. An angle φ between the central axis L and the chamfered circumferential edge in the range of 15-45 degrees appears to be sufficient.

A second exemplary embodiment of a cast mould 10 is shown in FIGS. 6-9, wherein for similar parts, the same reference numerals are used. The second exemplary embodiment involves a cast mould 10 for manufacturing an intraocular lens. It is clear that the intraocular lens that is manufactured with this second exemplary embodiment of the cast mould 10 will have two convex optical surfaces while the first exemplary embodiment which is shown in FIGS. 1-4 and FIG. 5 leads to a contact lens with a concave and an opposite convex optical surface. A further important difference between the first and the second exemplary embodiment of the cast mould 10 is that with the second exemplary embodiment, also in the first cast mould 12 an annular plastic film 21 connects a central part, which bears the optically accurately defined surface 14, to an outer part which comprises, inter alia, the support rib 17 and the outer edge 19 and thus forms a thin-walled flexible connection 21. For the thickness of thin-walled flexible connection 21 it holds, just as indicated hereinabove for the thin-walled flexible connection 30, 30a, 30b of the second cast mould half 14, that it is less than 0.2 times the thickness, and preferably even less than 0.1 times the thickness of wall parts which bound the flexible thin-walled connection 21. A bounding wall part is, for example, the central part with the optically accurately defined surface 14. Another bounding wall part is, for instance, the outer part mentioned that comprises, inter alia, the support rib 17 and the outer edge 19.

Figure 10:
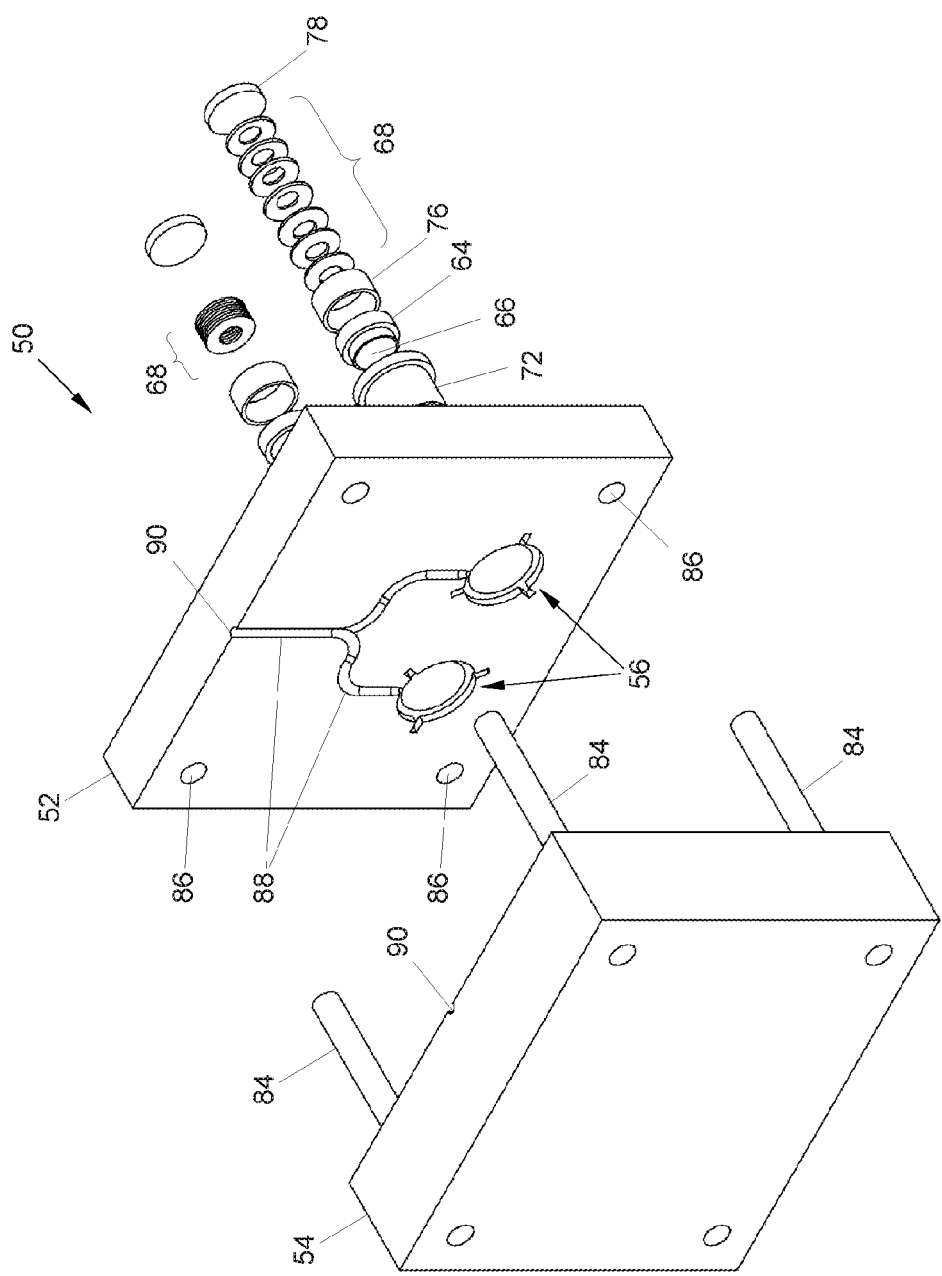
FIG. 10 shows a first perspective, exploded view of an exemplary embodiment of an injection mould for the purpose of the manufacture of a cast mould.
Figure 11:
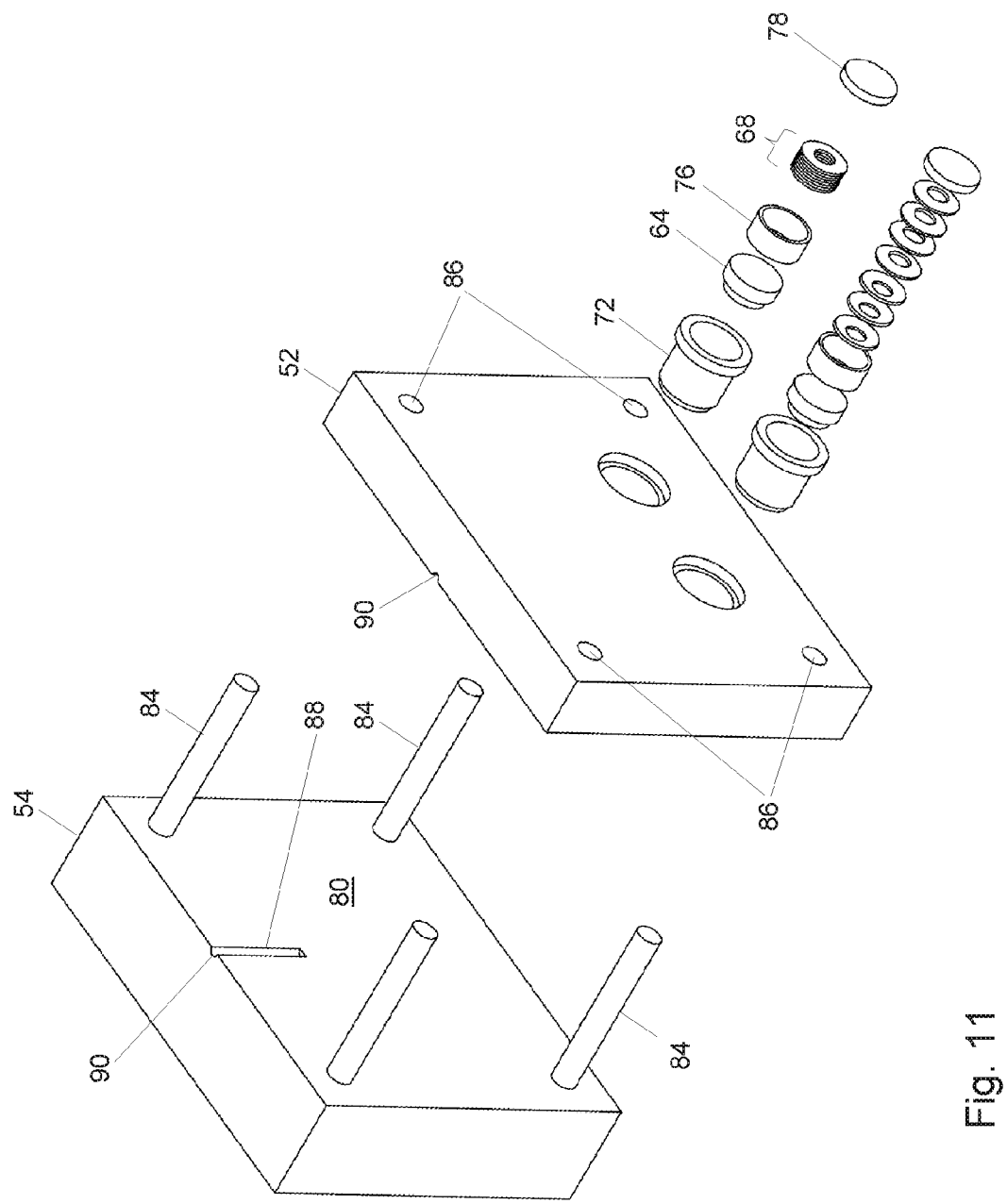
FIG. 11 shows a second perspective, exploded view of the injection mould represented in FIG. 10.
Figure 12:
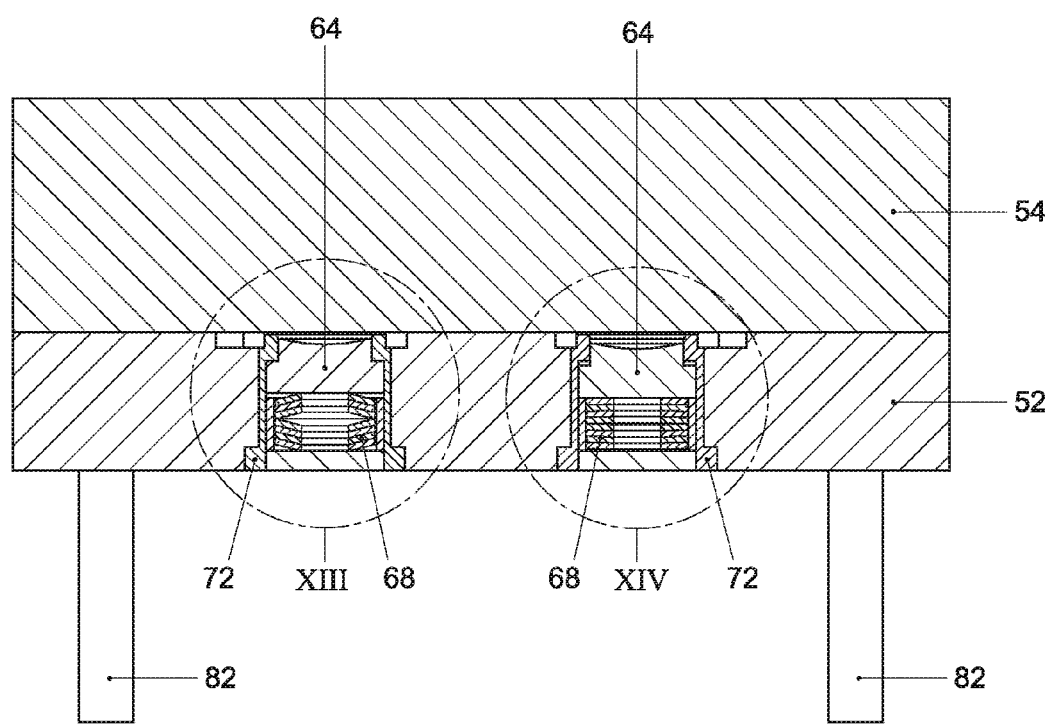
FIG. 12 shows a cross-sectional view of the injection mould of FIGS. 10 and 11.
Figure 13:
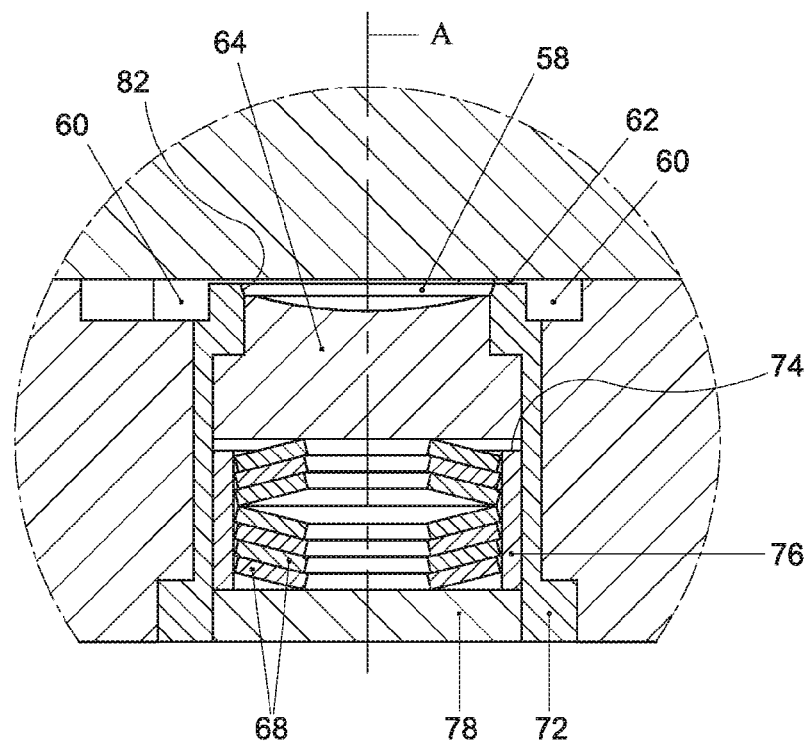
FIG. 13 shows detail XIII of FIG. 12.
Figure 14:
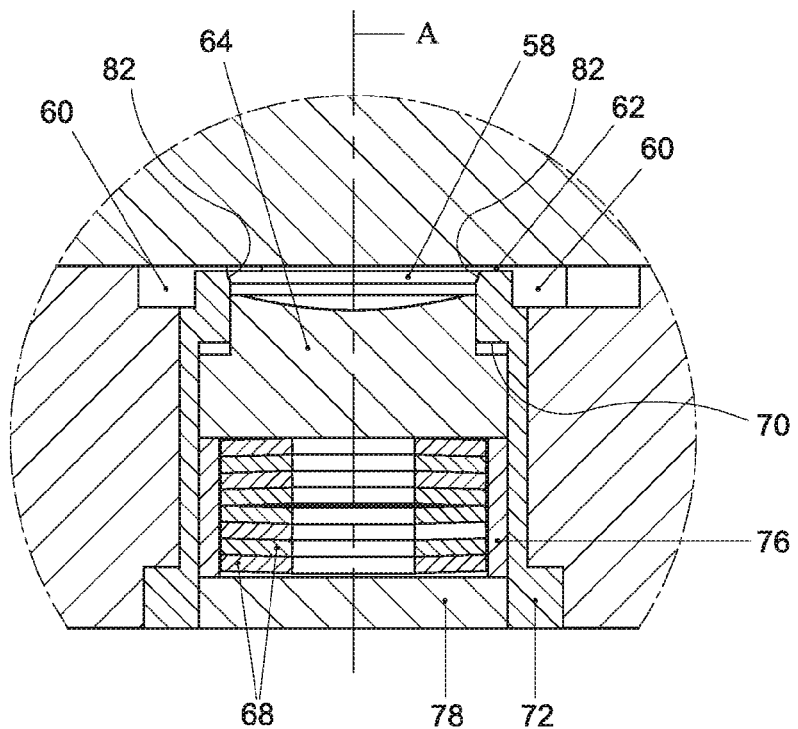
FIG. 14 shows detail XIV of FIG. 12.

FIGS. 10-14 show an example of an embodiment of an injection mould 50 for the manufacture of a cast mould 10 for manufacturing contact lenses or intraocular lenses. FIGS. 10 and 11 show the injection mould 50 in exploded view from different viewpoints. FIG. 12 shows a cross-sectional view of the injection mould 50 in assembled and closed condition. FIGS. 13 and 14 shows details of the injection mould 50 in two different conditions which will be reverted to later. The injection mould is provided with a first injection mould half 52 and a second injection mould half 54. The injection mould 50 is provided with at least one injection mould cavity 56 for manufacturing the second cast mould half 20. The injection mould 56 is formed when the two injection mould halves 52, 54 are in a moved together, closed position. A possibility of setting up the two injection mould halves 52, 54 movably relative to each other is formed by the guide pins 84 which are fixedly connected to the second injection mould half 54. The first injection mould half 52 is provided with guide holes 86 in which the guide pins 84 are fittingly and slideably received. This is only one possible solution for setting up the injection mould halves 52, 54 relative to each other in a manner movable towards and away from each other. Towards each injection mould cavity 56 runs a plastic supply channel 88. To a supply opening 90, an outflow opening of an extruder (not shown) can be connected. Each injection mould cavity 56 is provided with a central part cavity 58, a bearing ring cavity 60, and a connecting cavity 62 which connects the central part cavity 58 to the bearing ring cavity 60. In the exemplary embodiment shown, the injection mould 50 is provided with two injection mould cavities 56. However, it is clear that the injection mould 50 can also be provided with one or with more than two injection mould cavities 56.

For each injection mould cavity 56, the injection mould 50 is provided with a plunger 64 associated with the injection mould cavity 56, which is set up in the first injection mould half 52 so as to be movable along a longitudinal central axis A of the plunger. The plunger 64 is provided with an end face 66 which faces the injection mould cavity 56 and bounds the central part cavity 58. With each injection mould cavity 56, further, spring means 68 are associated which are biased such that the spring action thereof urges the plunger 64 in the direction of the central part cavity 58 towards a pressed-in position. As each injection mould cavity 56 has its own plunger 64 and its own spring means 68, it is effected that in each injection mould cavity 56 the plunger compensates for the shrinkage occurring in the respective injection mould cavity 56. As a result of this independent compensation per injection mould cavity 56, in each injection mould cavity 56 a continuous contact between the plunger 64 and the liquid and curing plastic present in the injection mould cavity 56 is effected. As a result, a second cast mould half 20 with an optical surface is obtained which is indeed accurately defined and which contains no cavitation bubbles or similar inaccuracies occurring as a result of shrinkage.

In one embodiment of the injection mould, of which an example is shown in FIGS. 10-14, the injection mould 50 is provided for each injection mould cavity 56 with a first stop 70 associated with this injection mould cavity 56, which stop forms a boundary for the movement of the plunger 64 towards the pressed-in position (see FIG. 13). In the exemplary embodiment, the first stop 70 is included in a first bush 72 which is included in the first injection mould half 52. The plunger 64 is provided with a stepped circumferential profile wherein the step 74 in the circumferential profile abuts against the first stop 70 when the plunger 64 is in the pressed-in position. FIG. 13 shows the plunger 64 in the pressed-in position. Instead of the first bush 72, the step 74 can also form an integral part of the first injection mould half 52. The first bush 72 is of advantage from a manufacturing-technical viewpoint. Moreover, by exchange of the bush 72, the inner diameter can be varied and hence the outer diameter of the plunger 64 included therein and hence the diameter of the optically accurately defined surface 24 of the second cast mould half 20.

In one embodiment of the injection mould 50, of which an example is shown in FIGS. 10-14, the injection mould 50 is provided for each injection mould cavity 56 with a second stop 74 associated with this injection mould cavity 56, which forms a boundary for the movement of plunger 64 from the pressed-in position towards a stop position moved away from the injection mould cavity 56. FIG. 14 shows the plunger in the stop position. In the represented example of this embodiment, the second stop 74 is formed by a second bush 76 which is included in the first bush 72. In the first bush 72 are included the plunger 64, the second bush 76 and the spring means 68. Then, the first bush 72 is sealed off with a sealing lid 78. The connection between the sealing lid 78 and the first bush 72 or, when the first bush 72 is omitted, the first injection mould half 52, can be formed by, for instance, thread or by a bayonet catch. Such a detachable connection of the sealing lid 78 enables simple exchange of the plunger 64 or replacement of the spring means 68. Replacement of the plunger 64 is advisable when another optically accurately defined surface 24 is wanted. Replacing the spring means 68 can be advisable when another spring constant is desired or upon breakage or slackening of the spring means 68.

In one embodiment, of which an example is shown in FIGS. 10-14, the spring means 68 can comprise one, or a stack of Belleville springs 68a, for instance Belleville springs 68a according to DIN 2093. The advantage of Belleville springs 68a is that in a very compact volume a very high spring constant can be realized. When the Belleville springs 68a according to DIN2093 are used with an outer diameter of 15 mm and a thickness of 0.8 mm, when thirteen Belleville springs 68a with the same orientation are stacked onto each other, a force of more than approximately 16.000 N is required for an impression of 0.4 mm. When the end face 66 of the plunger 64 has a surface of a good 1.1 cm$^2$, a pressure of 1450 bar is required in the injection mould cavity 58 for bringing the plunger into the stop position in which the Belleville spring packet of thirteen Belleville springs is completely compressed. This is a filling pressure which is feasible in a suitable manner with the right injection moulding machine. With such a filling pressure, furthermore, a rapid filling of the injection mould cavity 56 is obtained, which is important to prevent the occurrence of setting of plastic in the connecting cavity 62 before the complete filling of the injection mould cavity 56 is realised.

The advantage of Belleville springs is further that through suitable stacking, the spring travel length and the spring constant can be varied. When two Belleville springs 68 with the same orientation are stacked onto each other, the force required for completely compressing the Belleville spring packet doubles. The spring travel length is equal to that of a single Belleville spring. When two Belleville springs 68 with opposite orientation are stacked onto each other, the force required for completely compressing the Belleville spring packet remains equal to the force required for compressing a single Belleville spring. However, the spring travel length doubles with such a stacking. Through suitable stacking of Belleville springs 68a, therefore, a desired spring travel length in combination with a desired compression force can be realised.

In an alternative embodiment, the spring means 68 can be configured as a coil spring.

For manufacturing a second cast mould half 20 with a chamfered circumferential surface 34 as described hereinabove, one embodiment of the injection mould 50 can be characterized in that the central part cavity 58 is bounded, on one side by the end face 66 of the plunger 64 and on an opposite side by a wall part 80 of the second injection mould half. A circumferential wall 82 of the central part cavity 58 is chamfered, such that a diameter of the central part cavity 58, viewed in the direction of the longitudinal central axis A of the plunger 64 from the plunger 64 to the second injection mould half 54, gradually increases.

For manufacturing the second cast mould 20 of the cast mould 10, a method is provided with comprises:
  providing an injection mould 50;
  bringing the two injection mould halves 52, 54 into the closed position;
  injecting plastic into the at least one injection mould cavity 56 at a pressure which is such that the plunger 64 is moved from the pressed-in position against spring action;
  ending the injection and then allowing the plastic to cure while the spring means 68 continuously urge the plunger 64 in the direction of the central part cavity 58 to compensate for shrinkage of the plastic in the central part cavity.

One embodiment of the method, in which the injection mould 50 which is utilized further comprises a second stop 74 associated with each injection mould cavity 56 and which forms a boundary for the movement of the plunger 64 from the pressed-in position to a stop position moved away from the injection mould cavity 56, is characterized in that the pressure at which the plastic is injected into the at least one injection mould cavity 56 is sufficient for moving the plunger 64 against the spring action of the spring means 68 against the second stop 74. Thus it is realized that a sufficient filling of the injection mould cavity 56 is obtained to be able to compensate the shrinkage occurring therein.

Once the cast mould 10 is available, with it, with the aid of the following method, a contact lens or an intraocular lens 92 can be manufactured. The method comprises:
  providing a first cast mould half 12 of a cast mould 10;
  using the method for manufacturing the second cast mould 20 utilizing the injection mould 50 for obtaining the second cast mould half 20 of the cast mould 10;
  filling the first cast mould half 12 with a plastic;
  placing the second cast mould half 20 on the first cast mould half 22 such that the second positioning means 26 engage the first positioning means 16-18 and then clamp the second cast mould half 20 onto the first cast mould half 12 under a bias;
  allowing the plastic to cure in the cast mould 10 for forming the lens 92;
  removing the second cast mould half 20; and
  sealing, with a seal 36, the first cast mould half 12 in which the lens 92 is located for forming a package from the first cast mould half 12 and the seal 36 in which package the lens is included.

The seal can be formed by, for instance, a foil 36 which is attached through sealing on an outer edge 19 of the first cast mould half 12. In an alternative elaboration, it is possible that the seal 36 is formed by a lid provided with a bayonet or thread provision which cooperates with a bayonet or thread provision on the first cast mould half 12.

In one embodiment of the method, prior to the provision of the seal 36, a liquid can be introduced into the cast mould half 12.

Although the above-described description of the injection mould related to an injection mould 50 for manufacturing the second cast mould half 20, the invention is not limited thereto. Also for manufacturing the first cast mould half 12, with advantage, an injection mould can be used where with each injection mould cavity a plunger with spring means is associated which serves for compensating shrinkage in the respective injection mould cavity.

Although the invention is represented and described in detail with reference to the drawing, this drawing and description should be regarded as a mere example. The invention is not limited to the embodiments described. Features which are described in the subclaims can be combined with each other. Reference numerals in the claims should not be construed as limitations of the claims but merely serve for clarification.

The invention claimed is:

1. A cast mould for the purpose of manufacturing a contact lens or an intraocular lens, the cast mould being provided with:
   a first cast mould half comprising:
      an optically accurately defined surface; and
      a first positioning mechanism; and
   a second cast mould half comprising:
      a central part with optically accurately defined surface;
      a bearing ring which surrounds the central part and which is provided with a second positioning mechanism which is designed for engagement of the first positioning mechanism for holding the cast mould under a bias in a closed position in which the first and the second cast mould halves are clamped onto each other, wherein a central axis (L) of the second cast mould half extends perpendicularly to the plane in which the bearing ring extends and intersects a centre of the bearing ring; and
      a thin-walled, flexible connection which extends between the bearing ring and the central part and which connects the central part with the bearing ring,
   wherein a wall thickness of the thin-walled, flexible connection is less than 0.2 times a thickness of the central part at the location of the central axis, and
   wherein the wall thickness of the thin-walled, flexible connection is less than 0.2 times a thickness of the bearing ring.

2. The cast mould according to claim 1, wherein the thin-walled, flexible connection is formed by an annular plastic film which is connected by an outer edge thereof to the bearing ring and which is connected by an inner edge thereof to the central part.

3. The cast mould according to claim 1, wherein the thin-walled, flexible connection is formed by a number of spokes which are each connected by a first end to the central part and are connected by a second end to the bearing ring.

4. The cast mould according to claim 1, wherein a wall thickness of the thin-walled, flexible connection is less than 0.1 times the thickness of the central part at the location of the central axis (L).

5. The cast mould according to claim 1, wherein the central part of the second cast mould half opposite the optically accurately defined surface is provided with a second main surface which extends substantially perpendicularly to the central axis (L) of the second cast mould half, wherein the central part is provided with a circumferential surface which extends between the optically accurately defined surface and the second main surface, wherein the circumferential surface is chamfered, such that a diameter of the central part, viewed in the direction of the central axis (L) from the second main surface towards the optically accurately defined surface, gradually decreases.

6. A method for manufacturing at least the second cast mould half of the cast mould according to claim 1, the method comprising the steps of:
   providing an injection mould which is provided with:
      a first injection mould half; and
      a second injection mould half;
   wherein the two injection mould halves in a moved together, closed position define at least one injection mould cavity for manufacturing the second cast mould half, each injection mould cavity being provided with:
      a central part cavity;
      a bearing ring cavity which surrounds the central part cavity; and with
      a connecting cavity which connects the central part cavity with the bearing ring cavity;
   wherein the injection mould for each injection mould cavity thereof is provided with:
      a plunger associated with the injection mould cavity, which is set up in the first injection mould half so as to be movable along a central axis (A) of the plunger, the plunger being provided with an end face facing the injection mould cavity and bounding the central part cavity; and with
      a spring associated with the injection mould cavity, which is under a bias such that the spring action thereof urges the plunger in the direction of the central part cavity towards a pressed-in position;
   the method further comprising:
   bringing the two injection mould halves into the closed position;
   injecting plastic into the at least one injection mould cavity at a pressure which is such that the plunger is moved from the pressed-in position against spring action;
   ending the injection and then allowing the plastic to cure while the spring continuously urges the plunger in the direction of the central part cavity to compensate for shrinkage of the plastic in the central part cavity.

7. The method according to claim 6, wherein the injection mould which is utilized further comprises:
   for each injection mould cavity a second stop associated with this injection mould cavity, which stop forms a boundary for the movement of the plunger from the pressed-in position to a stop position moved away from the injection mould cavity;
   wherein in the method, the pressure at which the plastic is injected into the at least one injection mould cavity is sufficient for moving the plunger against the spring action of the spring against the second stop.

8. A method for manufacturing a contact lens or an intraocular lens, comprising:
   providing a cast mould, the cast mould being provided with:
      a first cast mould half comprising:
         an optically accurately defined surface; and
         a first positioning mechanism; and
      a second cast mould half comprising:
         a central part with optically accurately defined surface;
         a bearing ring which surrounds the central part and which is provided with a second positioning mechanism which is designed for engagement of the first positioning mechanism for holding the cast mould under a bias in a closed position in which the first and the second cast mould halves are clamped onto each other, wherein a central axis (L) of the second cast mould half extends perpendicularly to the plane in which the bearing ring extends and intersects a centre of the bearing ring; and a thin-walled, flexible connection which extends between the bearing ring and the central part and which connects the central part with the bearing ring, wherein a wall thickness of the thin-walled, flexible connection is less than 0.2 times a thickness of the central part at the location of the central axis, and wherein the wall thickness of the thin-walled, flexible connection is less than 0.2 times a thickness of the bearing ring;

using the method according to claim 6 utilizing an injection mould, wherein the injection mould is provided with:
  a first injection mould half;
  a second injection mould half; and
  at least one injection mould cavity for manufacturing the second injection mould half which cavity is formed when the two injection mould halves are in a moved together, closed position, wherein each injection mould cavity is provided with:
    a central part cavity;
    a bearing ring cavity; and
    a connecting cavity which connects the central part cavity to the bearing ring cavity;
  wherein the injection mould for each injection mould cavity is provided with:
    a plunger, associated with the injection mould cavity, which is set up in the first injection mould half so as to be movable along a central axis (A) of the plunger, the plunger being provided with an end face facing the injection mould cavity and bounding the central part cavity; and with
    a spring, associated with the injection mould cavity, which is under a bias such that the spring action thereof urges the plunger in the direction of the central part cavity towards a pressed-in position;

filling the first cast mould half with a plastic;

placing the second cast mould half on the first cast mould half such that the second positioning mechanism engages the first positioning mechanism and then clamping the second cast mould half on the first cast mould half under a bias;

allowing the plastic to cure in the cast mould for forming the lens;

removing the second cast mould half; and sealing with a seal the first cast mould half in which the lens is located for forming a package from the first cast mould half and the seal in which package the lens is included.

9. The method according to claim 8, wherein prior to the provision of the seal a liquid is introduced into the first cast mould half.

10. The cast mould according to claim 2, wherein a wall thickness of the thin-walled, flexible connection is less than 0.1 times the thickness of the central part at the location of the central axis (L).

11. The cast mould according to claim 3, wherein a wall thickness of the thin-walled, flexible connection is less than 0.1 times the thickness of the central part at the location of the central axis (L).

12. The cast mould according to claim 2, wherein the central part of the second cast mould half opposite the optically accurately defined surface is provided with a second main surface which extends substantially perpendicularly to the central axis (L) of the second cast mould half, wherein the central part is provided with a circumferential surface which extends between the optically accurately defined surface and the second main surface, wherein the circumferential surface is chamfered, such that a diameter of the central part, viewed in the direction of the central axis (L) from the second main surface towards the optically accurately defined surface, gradually decreases.

13. The cast mould according to claim 3, wherein the central part of the second cast mould half opposite the optically accurately defined surface is provided with a second main surface which extends substantially perpendicularly to the central axis (L) of the second cast mould half, wherein the central part is provided with a circumferential surface which extends between the optically accurately defined surface and the second main surface, wherein the circumferential surface is chamfered, such that a diameter of the central part, viewed in the direction of the central axis (L) from the second main surface towards the optically accurately defined surface, gradually decreases.

14. The cast mould according to claim 4, wherein the central part of the second cast mould half opposite the optically accurately defined surface is provided with a second main surface which extends substantially perpendicularly to the central axis (L) of the second cast mould half, wherein the central part is provided with a circumferential surface which extends between the optically accurately defined surface and the second main surface, wherein the circumferential surface is chamfered, such that a diameter of the central part, viewed in the direction of the central axis (L) from the second main surface towards the optically accurately defined surface, gradually decreases.

\* \* \* \* \*